United States Patent [19]
Hellerbach et al.

[11] 3,963,777
[45] June 15, 1976

[54] 1-POLYHYDROXY ALKYL-1,4-BENZODIAZEPIN-2-ONES

[75] Inventors: Joseph Hellerbach, Basel; Henri Hoffmann; Guido Zanetti, both of Reinach, all of Switzerland

[73] Assignee: Hoffmann-La Roche Inc., Nutley, N.J.

[22] Filed: Oct. 20, 1975

[21] Appl. No.: 624,132

Related U.S. Application Data

[62] Division of Ser. No. 397,043, Sept. 13, 1973, abandoned.

[52] U.S. Cl.............................. 260/562 N; 60/562 P
[51] Int. Cl.² ........................................ C07C 103/32
[58] Field of Search ...... 260/562 N, 562 P, 239.3 D

[56] References Cited
UNITED STATES PATENTS

| | | | |
|---|---|---|---|
| 3,784,542 | 1/1974 | Hellerbach et al. | 260/562 N |
| 3,886,214 | 5/1975 | Hellerbach et al. | 260/562 N |

*Primary Examiner*—C. Davis
*Attorney, Agent, or Firm*—Samuel L. Welt; George M. Gould; Frank P. Hoffman

[57] ABSTRACT

Novel 1,4-benzodiazepin-2-ones bearing a polyhydroxyalkyl group in the 1-position are disclosed. These 1-substituted benzodiazepins are useful as muscle relaxant, anti-convulsant and sedative agents.

1 Claim, No Drawings

1-POLYHYDROXY ALKYL-1,4-BENZODIAZEPIN-2-ONES

This is a division of application Ser. No. 397,043 filed Sept. 13, 1973, now abandoned.

DETAILED DESCRIPTION OF THE INVENTION

The present invention relates to 1-substituted-1,4-benzodiazepines. More particularly, this invention covers 1,4-benzoidiazepin-2-ones substituted in the 1-position with a polyhydroxyalkyl group. This invention further comprehends processes for making these novel benzodiazepines and novel intermediates used in these processes.

More specifically, the compounds of the present invention are selected from the group consisting of compounds of the formula

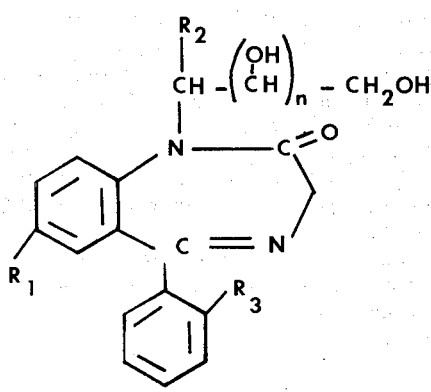

wherein
$R_1$ signifies halogen;
$R_2$ signifies hydrogen or lower alkyl;
$R_3$ signifies hydrogen or halogen;
n is an integer from 1–2
and the pharmaceutically acceptable acid addition salts thereof.

As used herein the term "lower alkyl" refers to straight and branched chain hydrocarbon groups containing from 1 to 7, preferably from 1 to 4, carbon atoms, such as, for example, methyl, ethyl, propyl, isopropyl, butyl and the like. The term "halogen" refers to all four forms thereof, i.e. bromine, chlorine, fluorine and iodine. The term "acyl" includes both lower alkanoyl and aroyl groups. The term "lower alkanoyl" refers to both straight and branched chain aliphatic carboxylic acid moieties containing from 2 to 7 carbon atoms such as acetyl, propionyl, butyryl and the like, with acetyl being preferred. The term "aroyl" refers to aromatic carboxylic acid moieties such as benzoyl and the like.

Preferred among the compounds of formula I above are those wherein the $R_1$ substituent is chlorine or iodine. When the $R_2$ substituent is lower alkyl, it is preferably methyl and when the $R_3$ substituent is halogen, it is preferably chlorine or fluorine.

The most preferred of the compounds of formula I above are:

7-chloro-1-(2,3-dihydroxypropyl)-5-(2-fluorophenyl)-1,3-dihydro-2H-1,4-benzodiazepin-2-one;
7-chloro-5-(2-fluorophenyl)-1,3-dihydro-1-(2,3,4-trihydroxybutyl)-2H-1,4-benzodiazepin-2-one;
7-chloro-1-(2,3-dihydroxypropyl)-1,3-dihydro-5-phenyl-2H-1,4-benzodiazepin-2-one; and
1-(2,3-dihydroxypropyl)-5-(2-fluorophenyl)-1,3-dihydro-7-iodo-2H-1,4-benzodiazepin-2-one.

The compounds of formula I above may be prepared following a variety of synthetic approaches.

A. In one such process aspect, the compounds of formula I can be prepared by cleaving off the protecting groups from a compound of the formula

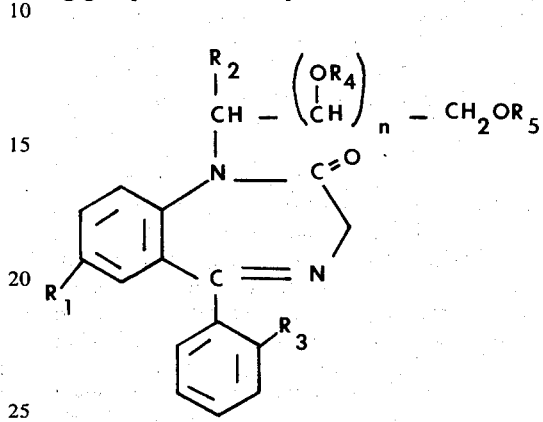

wherein $R_1$–$R_3$ and n are as described above, and $R_4$ and $R_5$ each signify a suitable protecting group, with the proviso that when n is 2, $R_4$ can also signify hydrogen.

The starting materials of formula II above thus bear on the substituent in the 1-position one or more protecting groups which are readily cleaved off to yield the corresponding benzodiazepine bearing a polyhydroxyalkyl group in the 1-position. Suitable protecting groups for the purpose include acyl groups such as acetyl, propionyl and benzoyl; the t-butyl group and the tetrahydropyranyl group. Two adjacent hydroxy groups can also be protected by a divalent protecting group such as an isopropylidene group.

Examples of starting materials of formula II which can be employed in this process aspect are:

7-chloro-1-(2,3-diacetoxypropyl)-5-(2-fluorophenyl)-1,3-dihydro-2H-1,4-benzodiazepin-2-one;
7-chloro-1-(2,3,4-triacetoxybutyl)-5-(2fluorophenyl)-1,3-dihydro-2H-1,4-benzodiazepin-2-one;
7-chloro-1-(2,3-diacetoxypropyl)-1,3-dihydro-5-phenyl-2H-1,4-benzodiazepin-2-one;
1-(2,3-diacetoxypropyl)-5-(2-fluorophenyl)-1,3-dihydro-7-iodo-2H-1,4-benzodiazepin-2-one; and
1-(4-acetoxy-2,3-dihydroxybutyl)-7-chloro-5-(2-fluorophenyl)-1,3-dihydro-2H-1,4-benzodiazepin-2-one.

The protecting groups found in the starting materials of formula II may be split off following conventional techniques.

The specific conditions under which the cleavage of the protecting group (s) is carried out are, of course, primarily dependent on the nature of the protecting group(s). In selecting such conditions, care must of course be taken to insure that the other substituents on the benzodiazepin ring are not affected. Thus, for example, an acyl protecting group such as an acetyl group can be cleaved off under alkaline conditions, whereas the cleavage of a tetrahydropyranyl group, a t-butyl group or a isopropylidene group may be carried out under acid conditions. Suitable acidic conditions can be obtained using hydrogen bromide in glacial acetic acid or, in the case of the t-butyl group, trifluoroacetic acid.

Examples of bases which can be used for the alkaline cleavage of an acyl group are alkali metal alcoholates such as sodium methylate and the like or ammonia. If an alkali metal alcoholate is employed to effect cleavage of the acyl group, this is conveniently carried out by taking up a compound of formula II bearing one or more acyl groups in a lower alkanol (e.g. methanol), adding thereto a solution of the alkali metal alcoholate (e.g. sodium methylate) in the same lower alkanol (e.g. methanol) and subsequently leaving the mixture to stand for about 1-5 hours at room temperature, if necessary, while stirring.

The cleavage of an acyl group by means of ammonia can be carried out, for example, by taking up a compound of formula II which contains one or more acyl groups in a suitable water-miscible organic solvent (e.g. a lower alkanol such as methanol), adding concentrated ammonia thereto and subsequently leaving the mixture to stand for some time (e.g 10 to 20 hours) at room temperature, if necessary, while stirring.

The starting materials of formula II above are novel and as such are a part of the present invention. The compounds of formula II wherein $R_4$ and $R_5$ signify a protecting group can be prepared by reacting a compound of the formula

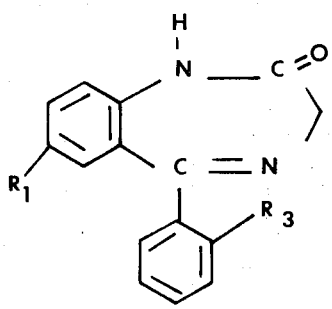

wherein $R_1$ and $R_3$ are as described above with a compound of the formula

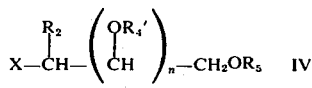

wherein $R_2$, $R_5$ and n are as described above, $R_4'$ signifies a protecting group and X is halogen or a suitable leaving group.

The reaction between the compounds of formula III and IV above is an alkylation reaction and thus it is expedient to first prepare the 1-alkali metal derivative of the formula III compound. This can be accomplished by treating the formula III compound with an alkali metal base or by allowing the reaction between the compounds of formulae III and IV to take place in the presence of such a base. Suitable bases for this purpose include alkali metal alcoholates such as sodium methylate and alkali metal hydrides such as sodium hydride. This reaction is conveniently effected in the presence of an inert organic solvent. Suitable solvents include dimethylformamide, dimethylsulfoxide, lower alkanols such as methanol, ethanol and the like.

In the compound of formula IV above, X can be a halogen group, preferably chlorine or bromine, or a suitable leaving group such as an arylsulfonyloxy group, e.g. tosyloxy, or a lower alkylsulfonyloxy group, e.g. mesyloxy.

The starting materials of formula II wherein n is 2 and $R_4$ represents hydrogen can be prepared by reacting a compound of formula III above with a compound of the formula

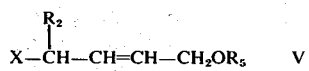

wherein X, $R_2$ and $R_5$ are as described above.

This reaction is carried out using the same reaction conditions described above for the reaction between the compounds of formulae III and IV above. The reaction product thus obtained is then subjected to an oxidative hydroxylation to yield the desired starting material of formula II. This oxidative hydroxylation can advantageously be carried out using potassium permanganate. In this case, it is expedient to effect the reaction in acetone/water, pyridine/water, acetone/triethylamine/water or acetone/buffer, e.g. sodium acetate/acetic acid buffer. This reaction is expediently carried out at a temperature in the range of from 0°C to room temperature.

B. In an alternate process aspect, the compounds of formula I above may be prepared by reacting a compound of formula III above with a compound of the formula

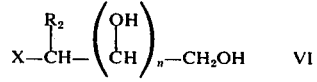

wherein X, $R_2$ and n are as described above.

The alkylation of the formula III compound with the compound of formula VI is carried out using the same reaction conditions described in process aspect A for the reaction between the compounds of formulae III and IV. Representative of the compounds of formula VI suitable for the purpose is 3-chloro-1,2-propanediol.

C. In a further process aspect, the compounds of formula I may be prepared by cyclizing a compound of the formula

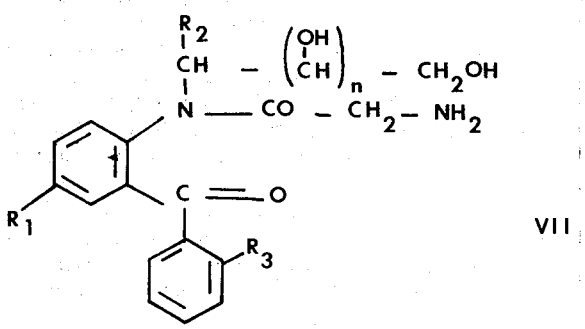

wherein $R_1 - R_3$ and n are as described above.

The cyclization of a compound of the type of formula VII is a reaction which is well known in benzodiazepine chemistry and is generally effected almost spontaneously. It can, if necessary, be brought about by prolonged standing and/or can be accelerated by the application of heat. It can be carried out in an alkaline, neutral or acidic medium; a neutral or, especially, an alkaline medium being preferred. This cyclization is conveniently carried out in an inert organic solvent; for example, a hydrocarbon (e.g. benzene, toluene and the like), a halogenated hydrocarbon (e.g. chloroform, methylene chloride, and the like) an ether (e.g. dioxane, tetrahydrofuran and the like), glacial acetic acid, and dimethylformamide. Temperature is not critical to this process aspect so that temperatures in the range of about room temperature to about 150°C, depending mainly upon the solvent system used, have been found to be convenient. The amino intermediate of formula VII is preferably not isolated from the reaction medium in which it is prepared but can by cyclized in situ under the reaction conditions described above to the desired benzodiazepine of formula I. Where it is desired to isolate a compound of formula VII prior to the cyclization rather than to allow the cyclization to proceed in situ, said compound is preferably isolated in the form of an acid addition salt thereof, for example, the hydrochloride or hydrobromide. The cyclization can then expediently be carried out by taking up the salt in question e.g. 2-amino-4'-chloro-N-(2,3-dihydroxypropyl)-2'-(2-fluorobenzoyl)acetanilide hydrochloride in a suitable solvent and then making the solution neutral or alkaline.

The starting materials of formula VII are novel and as such form a part of the present invention. These compounds are conveniently prepared from compounds of the general formula

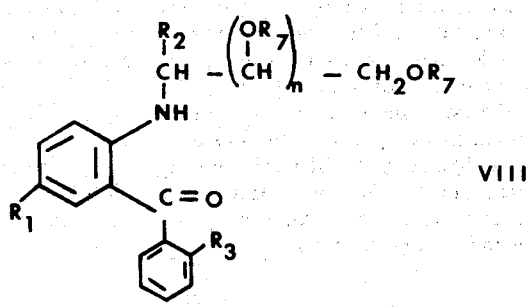

VIII wherein $R_1$, $R_2$, $R_3$ and n are as described above and $R_7$ represents hydrogen or a readily cleavable protecting group.

Examples of compounds of formula VIII are 5-chloro-2-[[(2,3-dihydroxypropyl)amino]-2'-fluorobenzophenone and 5-chloro-2-[(2,2-dimethyl-1,3-dioxolan-4yl)methyl amino]]-2'-fluorobenzophenone. The preparation of starting materials of formula VII from compounds of formula VII is carried out by introducing an amminoacetyl substituent onto the anilino-nitrogen atom and then cleaving off any protecting groups present. This introduction of an aminoacetyl substituent can be carried out following conventional techniques. Representative of such techniques are the reaction of the formula VIII compound:

1. With glycine chlorde hydrochloride;
2. With a carbobenzoxyglycine halide and subsequent cleavage of the carbobenzoxy group;
3. With azidoacetyl chloride or with chloroacetyl chloride and subsequent treatment with sodium azide. This accomplishes introduction of an azidoacetyl group, which can then be reduced to the desired amino group.

The cleavage of protecting groups present, can be effected using the procedures described in process aspect A above.

The compounds of formula VIII can be prepared by condensing a benzophenone of the general formula

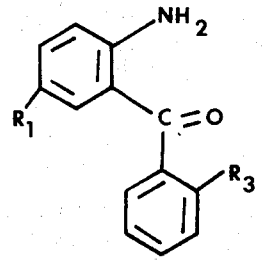

IX wherein $R_1$ and $R_3$ are as described above with benzaldehyde to give a corresponding benzal compound, quaternizing this benzal compound by reaction with a compound of formula VI or IV, then cleaving off the benzal group and, if desired, introducing or removing protecting groups.

D. In a further process aspect, the compounds of formula I above may be prepared by deoxidizing a compound of the formula

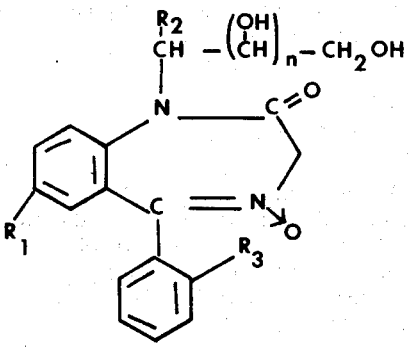

X wherein $R_1 - R_3$ and n are as described above.

The deoxidation of a compound of formula X is carried out according to methods which are customary for the conversion of a nitrone into the corresponding imine. It will be appreciated that the starting materials of formula X contain, in addition to the nitrone group, other reactive groups (especially the hydroxy groups on the substituent present in the 1-position) and that, accordingly, the particular deoxidation method chosen must be one in which such other reactive groups are not affected. This deoxidation is conveniently carried out by a mild catalytic hydrogenation, preferably using Raney-nickel as the catalyst, and in the presence of an inert organic solvent such as a lower alkanol, for example, methanol or ethanol, or an ether, for example dioxane or ethyl acetate. Temperature is not critical to this process aspect so that the reaction is expediently effected at room temperature.

The starting materials of formula X are novel and as such form a part of the present invention. These compounds can be prepared by introducing the desired substituent into a compound of the general formula

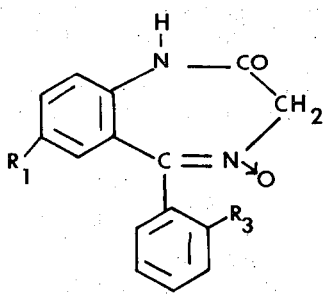

XI wherein $R_1$ and $R_3$ are as described above

This can be carried out, for example, according to one of the following methods:
1. reaction of the formula XI compound with a compound of formula VI in a manner analogous to that described earlier in connection with process aspect B.;
2. reaction of the formula XI compound with a compound of formulae IV or V in a manner analgous to that described earlier in connection with process aspect A. and, if necessary, subjecting the product to oxidative hydroxylation as described in process aspect A. and subsequently cleaving off the protecting group(s) in a manner analogous to that described earlier in connection with aspect A.;
3. reaction of the formula XI compound with a compound of the general formula

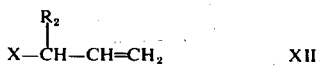

XII wherein X and $R_2$ are as described above
in a manner analogous to that described earlier in connection with process aspect A. and subsequently subjecting the product to an oxidative hydroxylation in a manner analogous to that described earlier in process aspect A.

The starting materials of formula X can also be prepared according to other methods, for example, by:
1. oxidizing a compound of formula II in which $R_4$ represents a protecting group (e.g. using a peracid such as m-chloro-perbenzoic acid) and subsequently cleaving off the protecting groups in a manner analogous to that described earlier in connection with process aspect A.;
2. oxidizing the starting material employed in process aspect F. described hereinafter and subsequently subjecting the product to an oxidative hydroxylation in a manner analogous to that described below in connection with process aspect F.;
3. reacting a compound of formula III with a compound of formula V in a manner analogous to that described earlier in connection with process aspect B., oxidizing the product obtained (e.g. using a peracid), subjecting the oxidation product to an oxidative hydroxylation in a manner analogous to that described hereinafter in process aspect F. and subsequently cleaving off the protecting group in a manner analogous to that described earlier in connection with process aspect A. E. In a further process aspect, the compounds of formula I above can be prepared by hydrolyzing and subsequently decarboxylating a compound of the formula

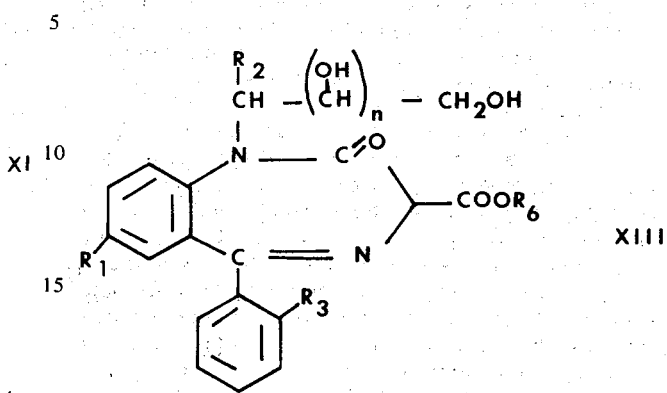

XIII wherein $R_1 - R_3$ and n are as described above and $R_6$ signifies lower alkyl.

The hydrolysis and decarboxylation of a compound of formula XIII can be carried out according to conventional methods. For example, a compound of formula XIII can be hydrolyzed under alkaline conditions to give the corresponding 3-carboxylic acid salt. The alkaline conditions can be provided, for example, by an alkali metal hydroxide (e.g. sodium hydroxide, potassium hydroxide etc.), an alkaline earth metal hydroxide (e.g. calcium hydroxide etc.), an alkali metal carbonate (e.g. potassium carbonate etc.) or a suitable tertiary organic base. The decarboxylation of the hydrolysis product is then effected slowly upon standing, more quickly upon heating and almost spontaneously upon acidification. When the hydrolysis is carried out under acidic conditions, the hydrolysis and decarboxylation are carried out in one step.

The starting materials of formula XIII are novel and as such form a part of the present invention. The compound of formula XIII can be prepared by reacting a compound of formula VIII above in which $R_7$ signifies a readily cleavable protecting group with a compound of the general formula

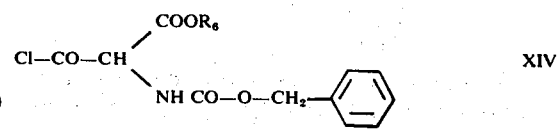

XIV wherein $R_6$ is as described above

The protecting groups in the resulting compound are than cleaved off and this product is cyclized in a manner analogous to that described in connection with process aspect C. above.

F. In another process approach to the compounds of formula I, a compound of the formula

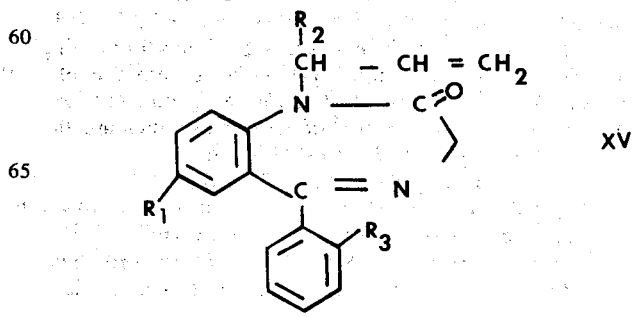

XV wherein $R_1 - R_3$ are as described above is oxidatively hydroxylated to yield the desired formula I compound wherein n signifies 1.

The manufacture of a 1,3-dihydro-2H-1,4-benzodiazepin-2-one of formula I in which n stands for 1 from a compound of formula XV represents an oxidative hydroxylation of an olefin to a corresponding diol, for which purpose there can be used a variety of customary methods. It will be appreciated that the starting materials of formula XV contain, in addition to the olefinic double-bond in the substituent present in the 1-position, other oxidizable groups (e.g. the nitrogen atom in the 4-position) and that, accordingly, the particular oxidative hydroxylation method chosen must be one in which such other oxidizable groups are not affected. The oxidative hydroxylation can advantageously be carried out, for example, using potassium permanganate. In this case, it is expedient to work in acetone/water, pyridine/water, acetone/triethylamine/-water or acetone/buffer solution (e.g. sodium acetate/acetic acid buffer). This oxidative hydroxylation is preferably carried out at a temperature between about 0°C and room temperature.

The starting materials of formula XV above are known compounds or can be preapared in analogy to the preparation of known compounds. Thus, for example, these compounds can be prepared by reacting a compound of formula III with a compound of formula XII (e.g. allyl bromide) in a manner analogous to that described earlier in connection with process aspect B. above.

G. In a further process aspect, the compounds of formula I above wherein n signifies 1 can be prepared by hydrolyzing a compound of the formula

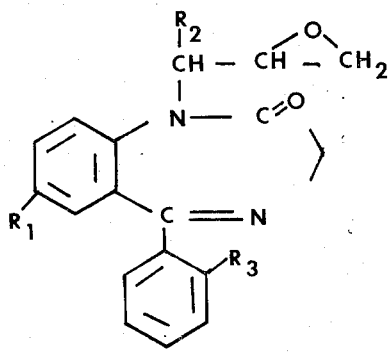

XVI wherein $R_1 - R_3$ are as described above

The conversion of the compound of formula XVI to the corresponding compound of formula I wherein n signifies 1 is effected using techniques known for the hydrolysis of an epoxide to the corresponding diol. This hydrolysis is preferably carried out under acidic conditions (e.g. by means of aqueous sulfuric acid, hydrochloric acid, etc.) and conveniently in the presence of a watermiscible organic solvent (e.g. a lower alkanol such as methanol).

The starting materials of formula XVI above are novel and as such form a part of the present invention. These compounds can be prepared by reacting a compound of formula III above with a compound of the general formula

XVII wherein X and $R_2$ are as described above

An example of a compound of formula XVII suitable for the present purposes is epichlorohydrin. The reaction between the compounds of formulae III and XVII above is carried out in a manner analogous to that described earlier in connection with process aspect B.

The compounds of formula I above are basic and thus can be converted into their pharmaceutically acceptable acid addition salts. Suitable salts include hydrochlorides, hydrobromides, phosphates, sulfates, citrates, acetates, succinates, maleates, p-toluene sulfonates, methanesulfonates and the like.

The compounds of formula I above and their pharmaceutically acceptable acid addition salts are useful as sedative muscle relaxant and anti-convulsant agents. The anti-convulsant activity of these compounds is demonstrated in the standard pentamethylenetetrazole test. For example, 7-chloro-1-(2,3-dihydroxypropyl)-5-(2-fluorophenyl)-1,3-dihydro-2H-1,4-benzodiazepin-2-one (Compound A), which has a $LD_{50}$ of 1250-2500 mg/kg (p.o.), exhibits an APR 2.0 of 5.6 mg/kg (p.o.) in the test for anticonvulsant activity in the pentetrazole test in accordance with the method of Orloff (Proc. Soc. Exptl. Biol. Med., 70, 254–257, 1949)[the term "APR 2.0" means that dosage in mg/kg of an anticonvulsant which causes a two-fold pentetrazole consumption in contrast to an untreated control group].

The sedative and muscle-relaxant activity of the compounds of formula I is demonstrated in the standard rotating rod test. In this test, the ability of mice to achieve a coordinated motor performance is investigated. After peroral administration of the test substance, the mice are placed upon a horizontal slowly rotating rod and the time they remain on the rod is recorded. The $ED_{50}$ is that dose which reduces the holding on period of the mice by 50% as compared to the holding on period prior to the administration of the test substance. In this test, Compound A exhibited an $ED_{50}$ of 5.1 mg/kg (p.o.), thus showing that this compound possesses sedative and muscle relaxant activity.

The 1-polyhydroxyalkylbenzodiazepines of formula I above are characterized by a high hydrophilicity when compared to known benzodiazepine derivatives. The compounds of the present invention thus have the advantage of being considerably more suited for incorporation into essentially aqueous parenteral preparations.

The benzodiazepine derivatives of formula I can be used as medicaments; for example, in the form of pharmaceutical preparations which contain them in association with a compatible pharmaceutical carrier. This carrier can be an organic or inorganic inert carrier material suitable for enteral, percutaneous or parenteral administration such as, for example, water, gelatin, gum arabic, lactose, starch, magnesium stearate, talc, vegetable oils, polyalkylene glycols, petroleum jelly etc. The pharmaceutical preparations can be made up in solid form (e.g. as tablets, dragees, suppositories or capsules), in semi-solid form (e.g. as salves) or in liquid form (e.g. as solutions, suspension or emulsions). If necessary, they may be sterilized and/or may contain adjuvants such as preserving, stabilizing, wetting or emulsifying agents, salts for variation of the osmotic pressure or buffers. They can also contain other therapeutically valuable substances. The dosage range should be determined by the individual exigencies of the case. However, a dosage of 0.1–5 mg/kg/day is recommended.

The following Examples illustrate the process provided by the invention:

EXAMPLE 1

2.4 g (50 mmol) of sodium hydride (50% dispersion) are suspended in 100 ml of absolute dimethylformamide and, with stirring and ice-cooling, there is added a solution of 14.4 g (50 mmol) of 7-chloro-5-(2-fluorophenyl)-1,3-dihydro-2H-1,4-benzodiazepin-2-one in 100 ml of absolute dimethylformamide. After the sodium hydride has been consumed, there are added 11.7 g (60 mmol) of 1-chloro-2,3-diacetoxypropane, whereafter the solution is heated to 80°–100°C for 18 hours with stirring and subsequently poured into 1 liter of ice-water. The precipitated product is extraced twice with 500 ml of ethyl acetate and the extracts are washed twice with 250 ml of water, combined, dried over magnesium sulfate and evaporated to dryness in a vacuum. The residue is chromatographed on a 20-fold amount of Silica gel with ethyl acetate and there is obtained a mixture of unreacted starting material and of 7-chloro-1-(2,3-diacetoxypropyl)-5-(2-fluorophenyl)- 1,3-dihydro-2H-1,4-benzodiazepin-2-one.

10.4 g of the foregoing mixture are dissolved in 100 ml of methanol and treated with a solution of 420 mg of sodium methylate in methanol. The solution is left to stand at room temperature for 2 hours and is then evaporated to dryness in a vacuum, whereafter the residue is treated with 300 ml of water and extracted twice with 250 ml of ethyl acetate. The extracts are washed twice with 200 ml of water, combined, dried over magnesium sulfate and evaporated to dryness in a vacuum. The residue is taken up in 50 ml of ethyl acetate and chromatographed on 200 g of silica gel. By elution with ethyl acetate there is obtained 7-chloro-1-(2,3-dihydroxypropyl)-5-(2-fluorophenyl)-1,3-dihydro-2H-1,4-benzodiazepin-2-one which is recrystallized from ethanol, m.p. 120°–122°C.

EXAMPLE 2

A solution of 21.6 g (75 mmol) of 7-chloro-5-(2-fluorophenyl)-1,3-dihydro-2H-1,4-benzodiazepin-2-one in 100 ml of absolute dimethylformamide is slowly added with stirring to an ice-cooled suspension of 3.6 g of sodium hydride (50% dispersion) in 50 ml of absolute dimethylformamide. The sodium hydride is consumed after 3 to 4 hours, and there are then added 23.4 g (75 mmol) of 1-bromo-2,3,4-triacetoxybutane, the mixture is heated to 100°C and left to stir at this temperature for 20 hours. Thereafter, the mixture is poured into 1.5 liters of icewater and extracted twice with 750 ml of ethyl acetate. The extracts are washed twice with 200 ml of water, dried over magnesium sulfate and evaporated to dryness in a vacuum. By chromatography of the residue on 1 kg of silica gel with ethyl acetate/methylene chloride (1:1) there is obtained, in addition to unreacted starting material, a mixture containing 7-chloro- 1-(2,3,4-triacetoxybutyl)-5-(2-fluorophenyl)-1,3-dihydro-2H-1,4-benzodiazepin-2-one.

18 g of the foregoing mixture are dissolved in 150 ml of methanol, whereafter 50 ml of concentrated ammonia are added thereto and the mixture is left to stand for 15 hours with gentle stirring. Thereafter, the mixture is evaporated to dryness (care being taken to ensure that all methanol is removed), the residue dissolved in 300 ml of ethyl acetate, washed twice with 100 ml of water and the wash-water re-extracted with 300 ml of ethyl acetate. The combined ethyl acetate extracts are dried over magnesium sulfate and then evaporated in a vacuum. Upon chromatography of the residue on 300 g of silica gel with ethyl acetate/methanol(9:1) there is firstly eluted 7-chloro-1-(2,3,4-triacetoxybutyl)-5-(2-fluorophenyl)-1, 3-dihydro-2H-1,4-benzodiazepin-2-one which can again be submitted to the 15-hours treatment with concentrated ammonia in methanol. There is subsequently eluted practically pure 7-chloro-5-(2-fluorophenyl)-1,3-dihydro-1-(2,3,4-trihydroxybutyl)-2H-1,4-benzodiazepin-2-one. After evaporation of the eluant, this product is taken up in a small amount of ethyl acetate, ethanolic hydrogen chloride solution is added thereto, the mixture is evaporated to dryness and the residue crystallized from a mixture of methanol and tetrahydrofuran, there being obtained 7-chloro-5-(2-fluorophenyl)-1,3-dihydro-1-(2,3,4-trihydroxybutyl)-2H-1,4-benzodiazepin-2-one hydrochloride of melting point 143°–145°C.

EXAMPLE 3

5.8 g of sodium hydride (50% dispersion; ca 0.1 mol) are suspended in 300 ml of absolute dimethylformamide and there is allowed to drop in, after about 1 hour with stirring, a mixture of 27 g (0.1 mol) of 7-chloro-1,3-dihydro-5-phenyl-2H-1,4-benzodiazepin-2-one and 300 ml of absolute dimethylformamide within 10 minutes. After stirring for 3 hours, 24.3 g (0.125 mol) of 1-chloro-2,3-diacetoxypropane are added thereto and the mixture is subsequently stirred for 70 hours at 80°C. Thereafter, the solvent is evaporated in a vacuum and the residue extracted twice with 500 ml of ethyl acetate, whereafter the extracts are washed twice with 300 ml of water, dried over magnesium sulfate, filtered and evaporated. Upon chromatography of the residue on 1 kg of silica gel with ethyl acetate, there is obtained a mixture of unreacted starting material and 7-chloro-1-(2,3-diacetoxypropyl)-1,3-dihydro-5-phenyl-2H-1,4-benzodiazepin-2-one.

The foregoing mixture is dissolved in 150 ml of absolute methanol, the solution obtained added dropwise to a methanolic sodium methylate solution (prepared from 920 mg of sodium and 100 ml of absolute methanol), the mixture obtained stirred for 2 hours at room temperature and then evaporated at 40°C in a vacuum. The residue is then extracted twice with 500 ml of ethyl acetate, whereafter the extracts are washed twice with 200 ml of water, dried over magnesium sulfate, filtered and evaporated. Upon chromatography of the residue on 500 g of silica gel with ethyl acetate, there is eluted firstly 7-chloro-1,3-dihydro-5-phenyl-2H-1,4-benzodiazepin-2-one, then impurities and finally 7-chloro-1-(2,3-dihydroxypropyl)-1,3-dihydro-5-phenyl-2H-1,4-benzodiazepin-2-one of melting point 151°–153°C.

EXAMPLE 4

A suspension of 4.8 g of sodium hydride (50% dispersion) in 100 ml of absolute dimethylformamide is treated dropwise at 0°C and with stirring with a solution of 38 g (0.1 mol) of 5-(2-fluorophenyl)-1,3-dihydro-7-iodo-2H-1,4-benzodiazepin-2-one. The mixture is stirred for 3 hours at 0°C, then 20 g (0.1 mol) of 1-chloro-2,3-diacetoxypropane are added, the mixture is heated to 100°C, stirred at this temperature for 18 hours and subsequently the dimethylformamide is evaporated in a vacuum. The residue is taken up in 600 ml of ethyl acetate, the solution is then washed three times with 200 ml of water, and the wash-water is re-extracted with 100 ml of ethyl acetate, whereafter the ethyl acetate solutions are combined, dried over magnesium sulfate, filtered and evaporated to dryness. The residue is chromatographed on 2 kg of silica gel with methylene chloride/ethyl acetate (3:1), whereby there is obtained a mixture of unreacted starting material and 1-(2,3-diacetoxypropyl)-5-(2-fluorophenyl)-1,3-dihydro-7-iodo-2H-1,4-benzodiazepin-2-one.

40.4 g of the foregoing mixture are dissolved in 100 ml of absolute methanol, treated with a solution of 340 mg of sodium methylate in 100 ml of absolute methanol stirred for 3 hours at 20°C and then the methanol evaporated. Upon chromatography of the residue on 1.2 kg of silica gel there is eluted, with ethyl acetate, 5-(2-fluorophenyl)-1,3-dihydro-7-iodo-2H-1,4-benzodiazepin-2-one and, with ethyl acetate/methanol (4:1), 1-(2,3-dihydroxypropyl)-5-(2-fluorophenyl)-1,3-dihydro-7-iodo-2H-1,4-benzodiazepin-2-one.

20 g of the latter compound are dissolved in 200 ml of ethyl acetate. The mixture is filtered, the filtrate is slowly treated with 4 ml of ethanolic hydrogen chloride solution with vigorous stirring, then evaporated to half of the volume and left to stand for 2 hours, whereafter the separated precipitate is filtered off and recrystallized twice from ethyl acetate/ethanol. There is obtained 1-(2,3-dihydroxypropyl)-5-(2-fluorophenyl)-1,3-dihydro-7-iodo-2H-1,4-benzodiazepin-2-one hydrochloride of melting point 171°C.

EXAMPLE 5

93 g of 1,4-dibromobut-2-ene are treated in 250 ml of dimethylformamide with 35.5 g of anhydrous sodium acetate and stirred for 1 hour at 100°C. The mixture is extensively freed from dimethylformamide on a rotary evaporator and the residue is partitioned between water and methylene chloride. The methylene chloride phase is dried over calcium chloride, filtered and concentrated. The residue is distilled under a water-jet vacuum, whereby the fractions are collected between 95° and 105°C at 10–15 mm; $n_D^{25}$=1.502. There is obtained 1-acetoxy-4-bromobut-2-ene as a colourless liquid.

7.2 g of 55% sodium hydride dispersion are washed three times with n-hexane, the well-stirred solution being allowed to settle and the supernatant n-hexane solution being removed under vacuum. The sodium hydride is then covered with 25 ml of dimethylformamide and treated dropwise with a solution of 43 g of 7-chloro-5-(2-fluorophenyl)-1,3-dihydro-2H-1,4-benzodiazepin-2-one in 125 ml of dimethylformamide. After diminishment of the hydrogen evolution, the mixture is stirred for a further 20 minutes at room temperature. Then 40 g of 1-acetoxy-4-bromobut-2-ene in 40 ml of dimethylformamide are added dropwise to the clear solution, whereby the reaction temperature rises to 50°C. After the addition, the mixture is stirred for a further 1 hour and then the mixture is extensively freed from dimethylformamide on a rotary evaporator. The residue is partitioned between ethyl acetate and water; the organic phase is washed with water, dried over magnesium sulfate and concentrated. The residue is chromatographed on silica gel with ethyl acetate/methylene chloride (1:1). The pure fractions are combined and yield 1-(4-acetoxy-2-butenyl)-7-chloro-5-(2-fluorophenyl)-1,3-dihydro-2H-1,4-benzodiazepin-2-one (identification by IR and NMR).

17 g of 1-(4-acetoxy-2-butenyl)-7-chloro-5-(2-fluorophenyl)-1,3-dihydro-2H-1,4-benzodiazepin-2-one are dissolved in 150 ml of acetone and treated dropwise with a solution of 8 g of potassium permanganate in 150 ml of water. After the potassium permanganate addition, the mixture is stirred for a further 25 minutes at room temperature and subsequently filtered off under vacuum from the precipitated manganese dioxide. The manganese dioxide is washed with acetone and the filtrate is freed from acetone on a rotary evaporator. The aqueous phase is extracted with ethyl acetate and the organic solution is washed with saturated aqueous sodium chloride solution, dried over magnesium sulfate, filtered and concentrated. There is obtained a viscous oil which contains the desired 1-(4-acetoxy-2,3-dihydroxybutyl)-7-chloro-5-(2-fluorophenyl)-1,3-dihydro-2H-1,4-benzodiazepin-2-one.

14 g of 1-(4-acetoxy-2,3-dihydroxybutyl)-7-chloro-5-(2-fluorophenyl)-1,3-dihydro-2H-1,4-benzodiazepin-2-one are dissolved in 30 ml of methanol, treated with 15 ml of 25% aqueous ammonia and stirred at room temperature for 16 hours. The mixture is then evaporated to dryness and chromatographed on silica gel with ethyl acetate/methanol (9:1). The pure fractions are combined and evaporated. There is obtained 7-chloro-5-(2-fluorophenyl)-1,3-dihydro-1-(2,3,4-trihydroxybutyl)-2H-1,4-benzodiazepin-2-one in the form of a foam.

EXAMPLE 6

5.3 g of sodium hydride (50% suspension, ca 0.11 mol) are suspended in 100 ml of absolute dimethylformamide in a 1.5 liter sulfonation flask fitted with a condenser, calcium chloride tube, stirrer, thermometer and dropping funnel, whereupon, after stirring briefly at room temperature, there is added dropwise within 10 minutes at 25°–30°C a mixture of 28.87 g (0.1 mol) of 7-chloro-5-(2-fluorophenyl)-1,3-dihydro-2H-1,4-benzodiazepin-2-one and 150 ml of absolute dimethylformamide. After stirring for 5 hours at room temperature, there are allowed to drop in, within 10 minutes at 25°–30°C, 33.2 g (0.3 mol) of 3-chloro-1,2-propanediol and the mixture is then stirred for 15 hours at 100°C. There is thus obtained a precipitate which is filtered off under vacuum and washed with ethyl acetate, whereafter the solvent is evaporated in a vacuum, 100 ml of water are added and the mixture is extracted twice with 500 ml of ethyl acetate each time. The ethyl acetate extracts are washed with 100 ml of water, dried over magnesium sulfate, filtered and concentrated in a vacuum. On standing for a considerable time, unreacted starting material crystallizes out from the oily residue. These crystals are filtered off and the filtrate is chromatographed on 1 kg of silica gel with ethyl acetate, there being firstly eluted additional starting material and subsequently the desired product.

After vacuum evaporation of the fractions containing the desired product, there are added 100 ml of ethyl acetate and a mixture of 10 ml of 28% ethanolic hydrochloric acid in 40 ml of ethyl acetate is carefully allowed to drop in with stirring, whereby there separate puffy yellow crystals which, however, soon change into an oil. After decantation of the ethyl acetate and treatment with absolute ethanol, 7-chloro-1-(2,3-dihydroxypropyl)-5-(2-fluorophenyl)-1,3-dihydro-2H-1,4-benzodiazepin-2-one hydrochloride crystallizes out; melting point 174°–175°C.

In order to obtain the free base, the foregoing hydrochloride is dissolved in 50 ml of water. The mixture is made alkaline with sodium bicarbonate and extracted twice with 150 ml of ethyl acetate, whereafter the extracts are washed with 50 ml of water, dried over magnesium sulfate, filtered and evaporated in a vacuum. The crude product remaining behind is recrystallized from alcohol, filtered off under vacuum and washed with ethyl acetate, there being obtained 7-chloro-1-(2,3-dihydroxypropyl)-5-(2-fluorophenyl)-1,3-dihydro-2H-1,4-benzodiazepin-2-one of melting point 118°–123°C.

EXAMPLE 7

25 g of 2-amino-5-chloro-2'-fluorobenzophenone, 30 g of benzaldehyde and 100 mg of zinc chloride are dissolved in 150 ml of toluene and boiled at reflux for 5 hours, the resulting water being azeotropically distilled off and collected in a water separator. Then 30 ml of 3-chloro-1,2-propanediol are added to the solution and the mixture is boiled for 24 hours. Then 100 ml of 3 N sulfuric acid are added and the mixture is subjected to a steam distillation. The residue which was not steam-volatilised is made alkaline with sodium hydroxide and extracted with ethyl acetate. The organic phase is washed with saturated sodium chloride solution, dried over magnesium sulfate, filtered and concentrated. By chromatography of the residue on silica gel with ethyl acetate, there is isolated 5-chloro-2-[(2,3-dihydroxypropyl)-amino]-fluorobenzophenone of melting point 111°–112°C. Benzylidene-[4-chloro-2-(2-fluorobenzoyl)-phenyl]-(2,3-dihydroxypropyl)-ammonium chloride and 2-(benzylidenamino)-5-chloro-2'-fluorobenzophenone, which result in the above reaction as intermediates, are not isolated.

3.3 g of 5-chloro-2-[(2,3-dihydroxypropyl)-amino]-2'-fluorobenzophenone are dissolved in methylene chloride and treated under anhydrous conditions with 2.6 g of glycyl chloride hydrochloride. The mixture is stirred for 2 hours at room temperature, then the methylene chloride is extensively distilled off, whereupon the residue is stirred for 30 minutes with 3 N hydrochloric acid. The acidic aqueous solution is extracted with ether, subsequently made alkaline with 3 N sodium hydroxide or concentrated ammonia and extracted with ethyl acetate. The ethyl acetate phase is washed with water, dried over magnesium sulfate, filtered and concentrated. The residue is chromatographed on silica gel with ethyl acetate, there being isolated 7-chloro-1-(2,3-dihydroxypropyl)-5-(2-fluorophenyl)-1,3-dihydro-2H-1,4-benzodiazepin-2-one of melting point 117°–118°C. During the aforementioned reaction, there is formed as an intermediate 2-amino-4'-chloro-N-(2,3-dihydroxypropyl)-2'-(2-fluorobenzoyl)-acetanilide, which is not isolated.

EXAMPLE 8

7.5 g of 5-chloro-2-[(2,3-dihydroxypropyl)-amino]-2'-fluorobenzophenone in 100 ml of acetone are treated with 2 ml of concentrated sulfuric acid and stirred for 20 hours. Then the solution is treated with solid sodium carbonate and filtered off under vacuum with the addition of a filtration adjuvant. The filtrate is concentrated and the residue is chromatographed on silica gel with ethyl acetate. There is obtained 5-chloro-2-[(2,2-dimethyl-1,3-dioxolan-4-yl)-methyl]-amino -2'-fluorobenzophenonone as an oil.

1 g of 5-chloro-2-{[(2,2-dimethyl-1,3-dioxolan-4-yl)-methyl]-amino}-2'-fluorobenzophenone are dissolved in 25 ml of absolute carbon tetrachloride, treated with 1.5 g of glycyl chloride hydrochloride and stirred for 1 hour at 25°C. Then the solvent is completely distilled off on a rotary evaporator and the residue is stirred with 25 ml of 3 N hydrochloric acid for 30 minutes. Subsequently the aqueous acidic solution is extracted with ether, made alkaline with 3 N sodium hydroxide or ammonia and extracted with ethyl acetate. The ethyl acetate phase is washed with water, dried over magnesium sulfate, filtered and evaporated. By chromatography on silica gel with ethyl acetate/methanol (9:1) there is isolated from the residue pure 7-chloro-1-(2,3-dihydroxypropyl)-5-(2-fluorophenyl)-1,3-dihydro-2H-1,4-benzodiazepin-2-one of melting point 116°–117°C. The compounds resulting as intermediates in the reaction 2-amino-4'-chloro-N-[(2,2-dimethyl-1,3-dioxolan-4-yl)-methyl]-2' -(2-fluorobenzoyl)-acetanilide and 2-amino-4'-chloro-N-(2,3-dihydroxypropyl)-2'-(2-fluorobenzoyl)-acetanilide are not isolated.

EXAMPLE 9

48 g of 55% sodium hydride dispersion are washed three times with n-hexane, whereby after stirring well and settling the supernatant n-hexane solution is evaporated under vacuum. The washed sodium hydride is covered with 150 ml of dimethylformamide and treated dropwise with a solution of 289 g of 7-chloro-5-(2-fluorophenyl)-1,3-dihydro-2H-1,4-benzodiazepin-2-one in 650 ml of dimethylformamide, a vigorous hydrogen evolution occuring. By external cooling, the reaction temperature is held at 30°C. After the addition, the mixture is stirred for a further 1 hour at room temperature. There are slowly added dropwise to the clear solution 133 g of allyl bromide in 150 ml of dimethylformamide, the reaction temperature rising to 50°C. After the addition, the mixture is stirred for a further 1 hour at room temperature. Then the solution is extensively freed from dimethylformamide on a rotary evaporator. The residue is partitioned between ethyl acetate and water. The ethyl acetate phase is washed with water, dried over magnesium sulfate, filtered and concentrated, the residue crystallizing spontaneously. The crystal brew is suspended in ether and filtered off under vacuum. There are obtained hard, yellowish crystals of melting poing 125°– 127°C. For analysis, a sample of the obtained 1-allyl-5-chloro-5-(2-fluorophenyl)-1,3-dihydro-2H-1,4-benzodiazepin-2-one is recrystallized from isopropanol; melting point 126°–127°C.

6.4 g of 1-allyl-7-chloro-5-(2-fluorophenyl)-1,3-dihydro-2H-1,4-benzodiazepin-2-one in 50 ml of chloroform are treated with 7 g of m-chloroperbenzoic acid and stirred for 16 hours at room temperature. Then the chloroform solution is washed with 1 N sodium bisulfite solution, with 2 N sodium hydroxide and with water. The organic phase is dried over calcium chloride, filtered and concentrated. The residue is recrystallized from ethanol and there is obtained 1-allyl-7-chloro-5-(2-fluorophenyl)-1,3-dihydro-2H-1,4-benzodiazepin-2-one 4-oxide of melting point 183°C.

3.3 g of 1-allyl-7-chloro-5-(2-fluorophenyl)-1,3-dihydro-2H-1,4-benzodiazepin-2-one 4-oxide are dissolved in acetone and treated dropwise with a solution of 1.6 g of potassium permanganate in water. After the addition, the mixture is stirred for a further 25 minutes at room temperature. Then the mixture is filtered off under vacuum from manganese dioxide, whereupon the manganese dioxide is washed with acetone and the filtrate is freed from acetone on a rotary evaporator. The aqueous phase is extracted with ethyl acetate and the organic phase is washed with water, concentrated and dried azeotropically with benzene. By chromatography on silica gel with ethyl acetate/methanol (9:1) there is isolated from the residue 7-chloro-1-(2,3-dihydroxypropyl)-5-(2-fluorophenyl)-1,3-dihydro-2H-1,4-benzodiazepin-2-one 4-oxide. For analysis, a sample is recrystallized from ethyl acetate; melting point 165°–166°C.

400 mg of 7-chloro-1-(2,3-dihydroxypropyl)-5-(2-fluorophenyl)-1,3-dihydro-2H-1,4-benzodiazepin-2-one 4-oxide are dissolved in 20 ml of methanol, treated with 200 mg of Raney nickel paste and shaken under hydrogen. After uptake of the calculated amount of hydrogen, the mixture is filtered off from catalyst and the clear filtrate concentrated. By chromatography on silica gel with ethyl acetate/methanol (9:1) there is isolated from the residue 7-chloro-1-(2,3-dihydroxypropyl)-5-(2-fluorophenyl)-1,3-dihydro-2H-1,4-benzodiazepin-2-one of melting point 117°–118°C.

EXAMPLE 10

2.4 g (0.011 mol) of[1-(benzyloxy)-formamido]-malonic acid monoethyl ester are dissolved in 50 ml of methylene chloride and treated at -30°C with 2.5 g (0.012 mol) of phosphorus pentachloride. After complete reaction of the phosphorus pentachloride, the clear solution is decanted off from a possible residue and treated under anhydrous conditions with 3.6 g (0.01 mol) of 5-chloro-2- {[2,2-dimethyl-1,3-dioxolan-4-yl)-methyl]-amino}-2'fluorobenzophenone in 50 ml of methylene chloride. After reaction for 20 minutes at room temperature, the solution is concentrated on a rotary evaporator. The residue is again dissolved in 50 ml of methylene chloride and extracted with 2 N potassium bicarbonate solution. The aqueous basic extracts are washed with methylene chloride and the combined methylene chloride phases are washed with water, dried over calcium chloride, filtered and concentrated.

The residue, containing crude 2-[1-(benzyloxy)-formamido]-4'-chloro-N-](2,2-dimethyl-1,3-dioxolan-4-yl)-methyl]-2-(2-fluorobenzoyl)-ethylmalonanilate, is dissolved in 25 ml of ca 30% hydrobromic acid in glacial acetic acid and stirred for 10 minutes at room temperature. The solution is then concentrated, whereupon the residue is dissolved in 25 ml of 2 N hydrochloric acid and is stirred in the cold for 20 minutes. The aqueous, acidic solution which contains the 2-amino-4'-chloro-N-(2,3-dihydroxypropyl)-2'-(2-fluorobenzoyl)-ethylmalonanilate hydrochloride is extracted with ether and made alkaline with ammonia. The separated base is taken up in methylene chloride, whereupon the organic phase is washed with water, concentrated and dried azeotropically with benzene. The residue is redissolved in toluene, treated with a trace of acetic acid and evaporated to dryness. The crude 7-chloro-1-(2,3-dihydroxypropyl)-5-(2-fluorophenyl)-2,3-dihydro-2-oxo-1H-1,4-benzodiazepin-2-carboxylic acid ethyl ester thus obtained is dissolved in methanol and treated with 3 N sodium hydroxide (or potassium carbonate solution) and stirred for 16 hours at room temperature. The solution is made acidic with 2-3 N hydrochloric acid and stirred for 10 minutes. The solution is extensively concentrated, redissolved in water and made alkaline with ammonia. The separated milky base is taken up in ethyl acetate. The ethyl acetate phase is washed with water, dried over magnesium sulfate, filtered and concentrated. By chromatography on silica gel with ethyl acetate/methanol (9:1), there is isolated from the residue pure 7-chloro-1-(2,3-dihydroxypropyl)-5-(2-fluorophenyl)-1,3-dihydro-2H-1,4-benzodiazepin-2-one; melting point 117°–118°C.

EXAMPLE 11

A solution of 16 g of potassium permanganate in 300 ml of water was added dropwise within 15 minutes at 10°C to a solution of 33.0 g of 1-allyl-7-chloro-5-(2-fluorophenyl)-1,3-dihydro-2H-1,4-benzodiazepin-2-one in 300 ml of acetone. After the potassium permanganate addition, the solution is stirred for a further 10 minutes. Then the mixture is filtered off by vacuum from the precipitated manganese dioxide and the manganese dioxide is washed with acetone. Subsequently the acetone is distilled off on a rotary evaporator. The remaining aqueous phase is extracted with ethyl acetate; the ethyl acetate solution is washed with saturated sodium chloride solution, dried over magnesium sulfate, filtered and concentrated. The residue is chromatographed on silica gel with ethyl acetate/methanol (9:1). The pure fractions are combined and evaporated. Crystallization from ethyl acetate yields pure 7-chloro-1-(2,3-dihydroxypropyl)-5-(2-fluorophenyl)-1,3-dihydro-2H-1,4-benzodiazepin-2-one of melting point 117°–118°C.

EXAMPLE 12

33.0 g of 1-allyl-7-chloro-5-(2-fluorophenyl)-1,3-dihydro-2H-1,4-benzodiazepin-2-one are dissolved in 200 ml of pyridine. 16 g of potassium permanganate in 300 ml of water are added dropwise within 20 minutes at room temperature to the well-stirred solution. After the potassium permanganate addition, the mixture is extensively concentrated on a rotary evaporator. The residue is briefly boiled out with ethyl acetate and filtered off under vacuum. The ethyl acetate filtrate is extracted with water, dried over magnesium sulfate, filtered and concentrated. The residue is dissolved in a small amount of ethyl acetate and seeded. By recrystallization of the first crystals there is obtained pure 7-chloro-1-(2,3-dihydroxypropyl)-5-(2-fluorophenyl)-1,3-dihydro-2H-1,4-benzodiazepin-2-one of melting point 117°–118°C.

The oxidation can also be carried out in acetone/triethylamine/water.

EXAMPLE 13

33.0 g of 1-allyl-7-chloro-5-(2-fluorophenyl)-1,3-dihydro-2H-1,4-benzodiazepin-2-one are dissolved in 300 ml of acetone. 16 g of potassium permanganate are dissolved in 300 ml of a buffer solution (sodium acetate/acetic acid buffer) and added dropwise at 10°C within 20 minutes and with stirring to the foregoing solution. After complete decolouration of the potassium permanganate solution, the mixture is filtered off under vacuum from the manganese dioxide, the manganese dioxide is washed with acetone and the residue is extensively freed from acetone on a rotary evaporator.

The remaining aqueous solution is treated with equal portions of methanol, toluene and cyclohexane and partitioned by stirring well. The aqueous/ methanolic phase is then extensively freed from methanol on a rotary evaporator and the remaining aqueous phase is extracted with ethyl acetate. The ethyl acetate solution is washed with saturated aqueous sodium chloride solution, dried over magnesium sulfate, filtered and concentrated. The residue is brought to crystallization by seeding from a small amount of ethyl acetate. By recrystallization of the first crystalline product from ethyl acetate there is obtained pure 7-chloro-1-(2,3-dihydroxypropyl)-5-(2-fluorophenyl)-1,3-dihydro-2H-1,4-benzodiazepin-2-one of melting point 117°–118°C.

EXAMPLE 14

0.5 g of 55% sodium hydride dispersion are washed three times with n-hexane, covered with 5 ml of dimethylformamide and treated dropwise with a solution of 3 g of 7-chloro-5-(2-fluorophenyl)-1,3-dihydro-2H-1,4-benzodiazepin-2-one in 25 ml of dimethylformamide. After the end of the hydrogen evolution, the mixture is stirred for a further 10 minutes. To the clear solution there are added dropwise 1.5 g of 1-chloro-2,3-epoxypropane (epichlorhydrin) in 2 ml of dimethylformamide. The mixture is stirred for 5 hours at room temperature and then the dimethylformamide is extensively distilled on a rotary evaporator. The residue is partitioned between water and ethyl acetate. The organic phase is washed with water, dried over magnesium sulfate, filtered and concentrated. The oily residue, which contains 7-chloro-1-(2,3-epoxypropyl)-5-(2-fluorophenyl)-1,3-dihydro-2H-1,4-benzodiazepin-2-one is processed further as a crude product.

1 g of crude 7-chloro-1-(2,3-epoxypropyl)-5-(2-fluorophenyl)-1,3-dihydro-2H-1,4-benzodiazepin-2-one is dissolved in 15 ml of methanol and 15 ml of 2 N sulfuric acid and stirred for 1 hour at 25°C. Then the solution is made alkaline with 3 N sodium hydroxide and the methanol is carefully distilled on a rotary evaporator. The aqueous phase is extracted with ethyl acetate and the ethyl acetate solution is washed with water, dried over magnesium sulfate, filtered and concentrated. By chromatography of the residue on silica gel with ethyl acetate/methanol (9:1) there is isolated 7-chloro-1-(2,3-dihydroxypropyl)-5-(2-fluorophenyl)-1,3-dihydro-2H-1,4-benzodiazepin-2-one of melting point 116°–117°C.

The following Examples illustrate pharmaceutical preparations containing the benzodiazepine derivatives provided by the present invention:

EXAMPLE A

Tablets of the following composition are manufactured:
7-Chloro-1-(2,3-dihydroxypropyl)-
-5-(2-fluorophenyl)-1,3-dihydro-2H-

| | |
|---|---|
| -1,4-benzodiazepin-2-one | 2.0 mg |
| Lactose | 95.0 mg |
| Maize starch | 50.0 mg |
| Talc | 2.7 mg |
| Magnesium stearate | 0.3 mg |
| Total Weight | 150.0 mg |

The benzodiazepine derivative and the adjuvant materials are blended and the mixture obtained is pressed to tablets.

EXAMPLE B

Tablets of the following composition are manufactured:
7-Chloro-1-(2,3-dihydroxypropyl)-
-5-(2-fluorophenyl)-1,3-dihydro-2H-

| | |
|---|---|
| -1,4-benzodiazepin-2-one | 5.0 mg |
| Lactose | 120.0 mg |
| Maize starch | 60.0 mg |
| Polyvinylpyrrolidone | 10.0 mg |
| Talc | 4.6 mg |
| Magnesium stearate | 0.4 mg |
| Total weight | 200.0 mg |

The benzodiazepine derivative and the adjuvant materials are blended and the mixture obtained is pressed to tablets.

EXAMPLE C

Capsules containing the following ingredients are manufactured:
7-Chloro-1-(2,3-dihydroxypropyl)-
-5-(2-fluorophenyl)-1,3-dihydro-2H-

| | |
|---|---|
| -1,4-benzodiazepin-2-one | 10.0 mg |
| Lactose | 101.0 mg |
| Maize starch | 20.0 mg |
| Talc | 9.0 mg |
| Total capsule content | 140.0 mg |

The benzodiazepine derivative and the adjuvant materials are blended and the mixture is machine-filled into hard gelatine capsules.

EXAMPLE D

Suppositories of the following composition are manufactured:

| | | |
|---|---|---|
| 7-Chloro-1-(2,3-dihydroxypropyl)-<br>-5-(2-fluorophenyl)-1,3-dihydro-2H-<br>-1,4-benzodiazepin-2-one | | 10.0 mg |
| Polyoxyethylene Vegetable Oil | 1.0% | |
| Propyleneglycol monostearate | 4.5% | q.s. for the total weight of 1 suppository |
| Saturated Vegetable Oil | 94.5% | |

The adjuvant materials are melted together, the benzodiazepine derivative is then added and the mixture blended until a homogeneous mixture is obtained. This mixture is then poured into suppository moulds of suitable size. After cooling, the suppositories are removed from the moulds and individually packed in metal foil.

EXAMPLE E

An injection solution of the following composition is manufactured:
7-Chloro-1-(2,3-dihydroxypropyl)-
-5-(2-fluorophenyl)-1,3dihydro-2H-

| | |
|---|---|
| -1,4-benzodiazepin-2-one | 10.0 mg |
| Alcohol (absolute) | 200.0 μl |
| Diethanolamine | 3.0 mg |
| 1 N hydrochloric acid ad pH 7.0 | q.s. |
| Water for injecton ad | 1.0 ml |

The benzodiazepine derivative is dissolved in absolute alcohol. After the addition of water for injection, the diethanolamine is added and the pH adjusted to 7.0 with 1 N hydrochloric acid. Finally, the mixture is made up with water for injection to the end volume. The injection solution is filled into colourless ampoules which are sterilized in an autoclave at 120°C.

EXAMPLE F

An injection solution of the following composition is manufactured:
7-Chloro-1-(2,3-dihydroxypropyl)-
-5-(2-fluorophenyl)-1,3-dihydro-2H-

| | |
|---|---|
| 7-Chloro-1-(2,3-dihydroxypropyl)--5-(2-fluorophenyl)-1,3-dihydro-2H--1,4-benzodiazepin-2-one | 5.0 mg |
| Alcohol (absolute) | 100.0 μl |
| Diethanolamine | 3.0 mg |
| 1 N hydrochloric acid ad pH 7.0 | q.s. |
| Water for injection ad | 1.0 ml |

The benzodiazepine derivative is dissolved in absolute alcohol. After the addition of water for injection, the diethanolamine is added and the pH adjusted to 7.0 with 1 N hydrochloric acid. Finally, the mixture is made up with water for injection to the end volume. The injection solution is filled into colourless ampoules which are sterilized in an autoclave at 120°C.

We claim:
1. A compound of the formula

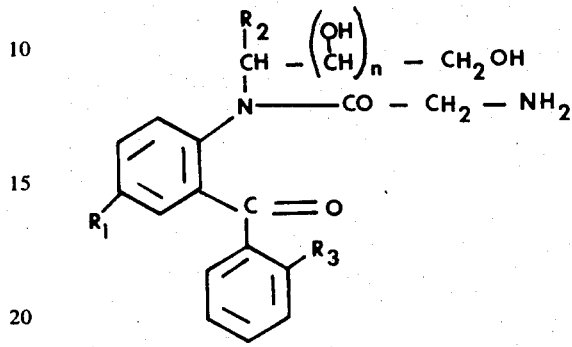

wherein $R_1$ signifies halogen, $R_2$ signifies hydrogen or lower alkyl, $R_3$ signifies hydrogen or halogen and $n$ is an integer from 1–2.

* * * * *